(12) United States Patent
Schutz et al.

(10) Patent No.: US 9,174,037 B2
(45) Date of Patent: Nov. 3, 2015

(54) IMPLANTED ACCESS PORT

(71) Applicant: Cendres + Metaux SA, Bienne (CH)

(72) Inventors: Daniel Schutz, Aarwangen (CH);
Jean-Marc Guenat, Bienne (CH);
Adrian Auderset, Nidau (CH); Hans Messerli, Bienne (CH); Christof Stieger, Bern (CH); Felix Frey, Kriechenwil (CH); Rudolf Hausler, Habstetten (CH)

(73) Assignee: Cendres + Mataux SA (CH)

( * ) Notice: Subject to any disclaimer, the term of this patent is extended or adjusted under 35 U.S.C. 154(b) by 380 days.

(21) Appl. No.: 13/678,197

(22) Filed: Nov. 15, 2012

(65) Prior Publication Data
US 2013/0072847 A1  Mar. 21, 2013

Related U.S. Application Data

(63) Continuation of application No. PCT/EP2010/057860, filed on Jun. 4, 2010.

(51) Int. Cl.
*A61M 37/00*  (2006.01)
*A61M 39/28*  (2006.01)
*A61M 39/02*  (2006.01)

(52) U.S. Cl.
CPC ......... *A61M 39/285* (2013.01); *A61M 39/0247* (2013.01); *A61M 2039/027* (2013.01); *A61M 2039/0258* (2013.01); *A61M 2039/0261* (2013.01); *A61M 2039/0264* (2013.01); *A61M 2039/0276* (2013.01); *A61M 2039/0282* (2013.01)

(58) Field of Classification Search
CPC .......... A61M 39/285; A61M 29/0247; A61M 2039/0258; A61M 2039/2061; A61M 2039/0264; A61M 2039/027; A61M 2039/0276; A61M 2039/2082
USPC .............................. 604/4.01–6.16, 8–10, 175
See application file for complete search history.

(56) References Cited

U.S. PATENT DOCUMENTS 4,108,173 A * 8/1978 Slivenko et al. .............. 604/175
2006/0047249 A1   3/2006 Shubayev et al.

FOREIGN PATENT DOCUMENTS

| EP | 0299547 A1 | 1/1989 |
|---|---|---|
| WO | WO-8103425 A1 | 12/1981 |
| WO | WO-2005023336 A2 | 3/2005 |
| WO | WO-2007051339 A1 | 5/2007 |

* cited by examiner

*Primary Examiner* — Philip R Wiest
(74) *Attorney, Agent, or Firm* — Blank Rome LLP

(57) ABSTRACT

Implantable access port for removal and/or return of fluids to a patient, comprising an internal conduit connectable at its proximal end to the access port and at its distal end to a vascular structure of the patient; an external conduit connectable at its proximal end to the access port and at its distal end to an extracorporeal device; and a transcutaneous coupling member destined to be anchored in a tissue of the patient and comprising a first valve system operable to be in an open or closed configuration; the coupling member further comprises a second valve system removably connectable to the first valve system and operable to be in an open or closed configuration, such as to establish fluid communication between the internal and external conduits when the first and second valve systems are connected and in open configuration.

26 Claims, 14 Drawing Sheets

IMPLANTED ACCESS PORT

REFERENCE DATA

The present application is a continuation of PCT Patent Application PCT/EP2010/057860 of Jun. 4, 2010, the content whereof are hereby incorporated by reference.

FIELD

The present disclosure relates to an implantable access port for removal and/or return of fluids to a patient. The implantable access is usable for establishing temporary access to blood vessels, an organ, a body lumen or cavity or any combination thereof of a human or animal, for the purpose of hemodialysis, drug delivery, nutrition delivery, urinary catheterism or any other supply or removal of fluids.

BACKGROUND

Access to a patient's lumen can be established by a variety of temporary and permanently implanted devices. However, despite several types of lumen access ports and devices proposed over recent years, body lumen access remains one of the most problematic areas in the treatment of patients requiring long-term access. Most simply, temporary access can be provided by the direct percutaneous introduction of a needle through the patient's skin and into a blood vessel. While such a direct approach is relatively straightforward and suitable for applications such as intravenous feeding, short term intravenous drug delivery and other applications which are limited in time, they are not suitable for hemodialysis and other extracorporeal procedures that must be repeated periodically and often for the patient's lifetime.

Haemodialysis patients commonly undergo a placement of one of the two, or both, widely accepted long-term vascular access options during the term of their treatment. It is estimated that 50% of hospitalization time of haemodialysis patients is related to problems of access to the vascular system of the human body.

On the one hand, WO 2005/023336 discloses a surgical placement of an arteriovenous synthetic graft connecting a patient's adjacent peripheral artery and vein to divert some of the arterial blood flow through the graft. The other is an arteriovenous fistula, a direct surgical connection between adjacent artery and vein with no synthetic conduit used. In both cases, the blood circulation is accessed with two needles inserted through the skin into either the synthetic graft in the former case, or the venous portion of an arteriovenous fistula in the latter scenario. Needle stick injuries and infections contribute to the loss of these types of accesses.

US 2006/0047249, by Shubayev and Elyav, proposes a percutaneous vascular access system. This system consists of a cylindrical device body having a pair of hollow nipples extending from the exterior to the interior and a rotatable inner core with two positions to open and close the connections. However, the fixation of such a device to the skin or other soft tissue of the body, i.e. as a tissue anchor according to US 2006/0047249, raises a number of problems, such as the danger of displacement during use caused by body movements or exposure to mechanic stress.

Bone implanted access devices have also be proposed. For example, WO 2007/051339 concerns an access port comprising a central cylindrical portion, and external and internal canal communicating through a valve. Here, the access port contains only one fluid canal and is destined to be implanted in a tooth-supporting bone.

SUMMARY

The present application discloses an access port which overcome at least some limitations of the prior art.

According to the embodiments, an implantable access port for removal and/or return of fluids to a patient, can comprise: an internal conduit adapted to be connected at its proximal end to the access port and at its distal end to a vascular structure of the patient; an external conduit adapted to be connected at its proximal end to the access port and at its distal end to an extracorporeal device; and a transcutaneous coupling member destined to be anchored in a tissue of the patient and comprising a first valve system operable to be in an open or closed configuration to establish or block fluidic communication to and from the internal conduit; characterized in that the coupling member further comprises a second valve system adapted to be removably connected to the first valve system and operable to be in an open or closed configuration to establish or block fluidic communication to and from the external conduit, such as to establish fluid communication between the internal and external conduits when the first and second valve systems are connected and in the open configuration In an embodiment, the first valve system can comprise a resilient valve conduit and a clamping device, the clamping device being adapted to apply a pressure on the resilient valve conduit to collapse it and set the first valve system in the closed configuration, and release the pressure allowing the resilient valve conduit to open, setting the first valve system in the open configuration.

In another embodiment, the first valve system comprises one or several passageways traversingly arranged in an inner core.

In yet another embodiment, the inner core can be rotated in a position where said one or several passageways are in fluidic communication with the internal conduit, setting the first valve system in the open configuration, and in another position where the fluidic communication between said one or several passageways and the internal conduit is blocked, setting the first valve system in the closed configuration.

In yet another embodiment, the second valve system comprises a membrane valve that can be operated in the open configuration by inserting the proximal end of the external conduit through the membrane valve, and in the closed configuration by removing the external conduit from the membrane valve.

In yet another embodiment, the coupling member further comprises a fixation unit for anchoring the coupling member to the tissue of the patient.

In yet another embodiment, the coupling member further comprises an auxiliary coupling member destined to be anchored in a tissue of the patient remotely form the coupling member and comprising the second valve system. The access port disclosed herein allows for an improved control of the fluidic communication within the port. The port can be manipulated more easily by selectively closing one of the valve systems. Moreover, bone anchoring of the implantable access results in the implantable access being more stable, suffering less or no movement, and is less prone to infection. An advantage of the access port disclosed herein is that the second valve system can be removed from the access port for cleaning and/or replacement purposes while the first valve system remains in the closed configuration. This diminishes the risk of having bacteria penetrating into the access port itself. Moreover, the first valve system tends to last much longer than the second valve system, retarding the time when the access port needs to be replaced compared with conventional access ports.

In the present disclosure, unless otherwise specified, the expression "proximal" means on the side of the access port, and the expression "distal" means away from the access port.

BRIEF DESCRIPTION OF THE DRAWINGS

The preferred embodiments will be better understood with the aid of the description of an embodiment given by way of example and illustrated by the figures, in which.

DETAILED DESCRIPTION OF THE PREFERRED EMBODIMENTS

Figure 1:
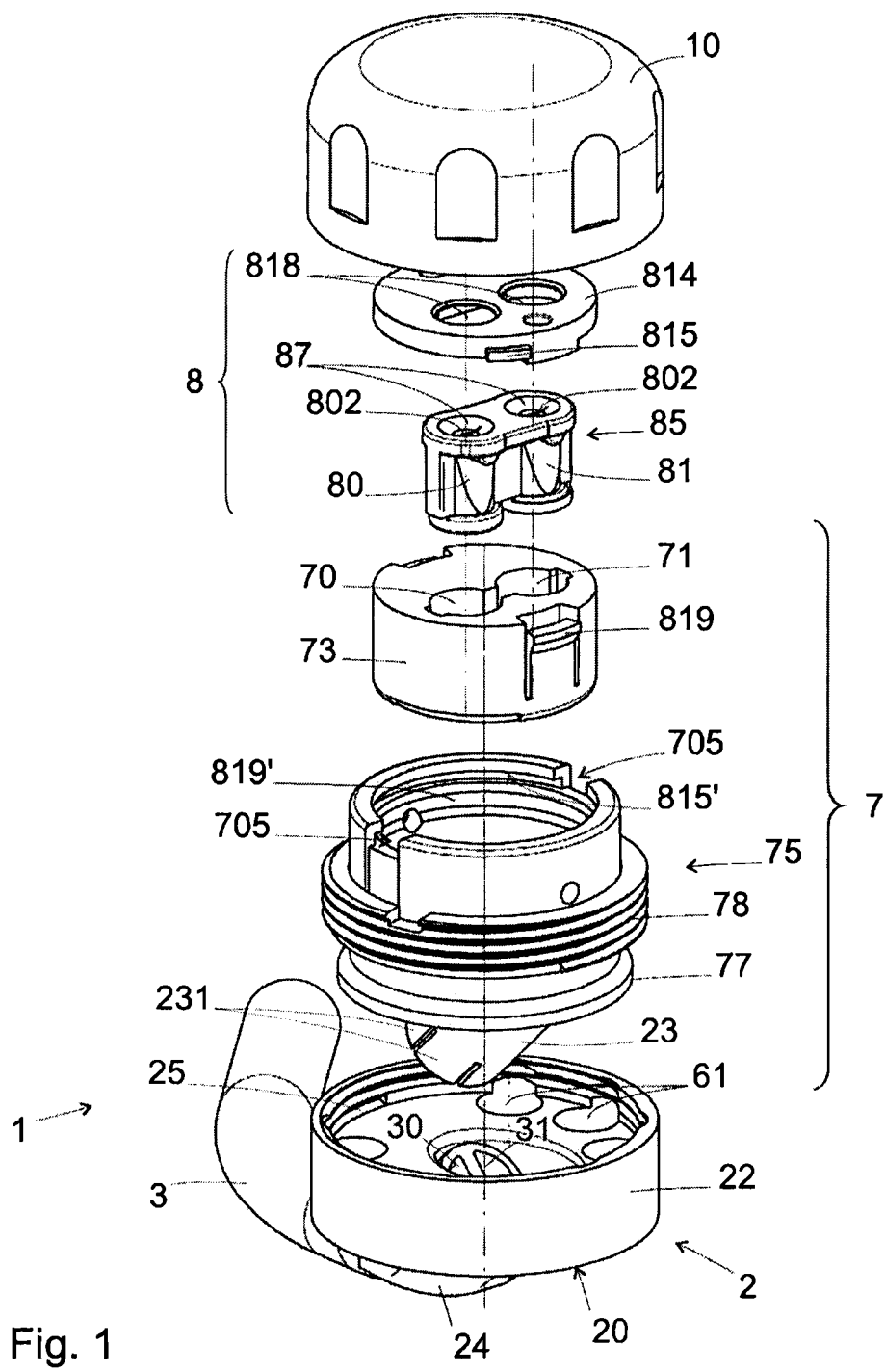
FIG. 1 shows an exploded view of an implantable access port comprising a first coupling member with a first valve system, and a second coupling member with a second valve system, according to an embodiment.
Figure 2:
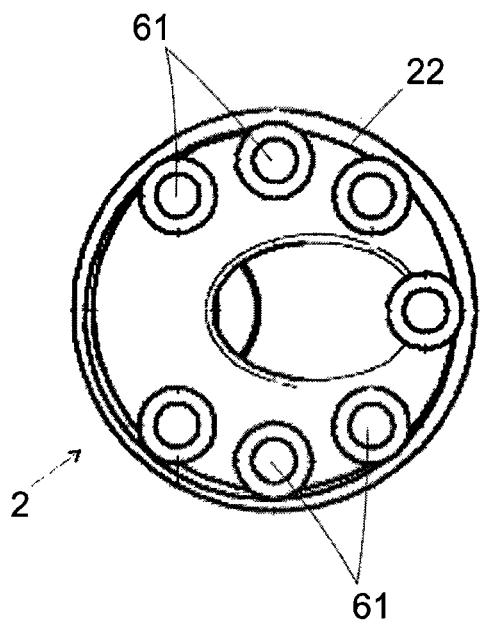
FIG. 2 represents a top view of the first coupling member according to an embodiment.

An exploded view of an implantable access port 1, for removal and/or return of fluids to a patient, is shown in FIGS. 1 to 5 according to an embodiment. The access port 1 comprises a transcutaneous coupling member 2 formed from base plate 20 and a wall portion 22 and extending from the base plate 20. The wall portion 22 can have a substantially cylindrical shape or any other shape. Preferably, the wall portion has a tapered shape. An outlet nozzle 24 protrudes from the coupling member 2, underneath the base plate 20. The coupling member 2 is adapted to be anchored to a bone of a patient (or another tissue) via a fixation unit. In the example of FIG. 1, the fixation unit comprises traversing holes 61 provided at the periphery of the base plate 20 and adapted to carry a screw (not shown) for anchoring the coupling member 2 by means of screws. A top view of the coupling member 2 is represented in FIG. 2 where the holes 61 and the outlet nozzle 24 can be easily seen.

In a preferred embodiment, the coupling member 2 is destined be anchored to a bone such as the hip, clavicle, sternum or any other section of the skeleton. More preferably, the coupling member 2 is destined to be permanently anchored to the mastoid, temporal or parietal bone. The coupling member 2 is preferably made in titanium or its alloy or in a biocompatible polymeric material such as PEEK or PEKK.

Figure 3:
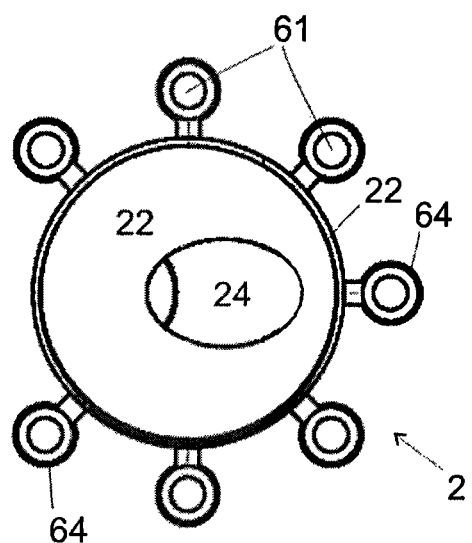
FIG. 3 represents a top view of the first coupling member according to another embodiment.

In another embodiment shown in FIG. 3, the fixation unit comprises a number of arms 64 attached to the coupling member 2 and provided with holes 61 for carrying a screw (not shown), for anchoring the coupling member 2 by means of screws. In this latter configuration, the number of arms 64 can vary, being typically three or more, depending on the size and intended placing. The arms 64 can be pivotal and inclinable to admit maximum of adaptation to the substrate to which they shall be screwed. Alternatively, the fixation unit can also comprise pins, wires, non-absorbable threads, cement or any other suitable fixation means.

Figure 7:
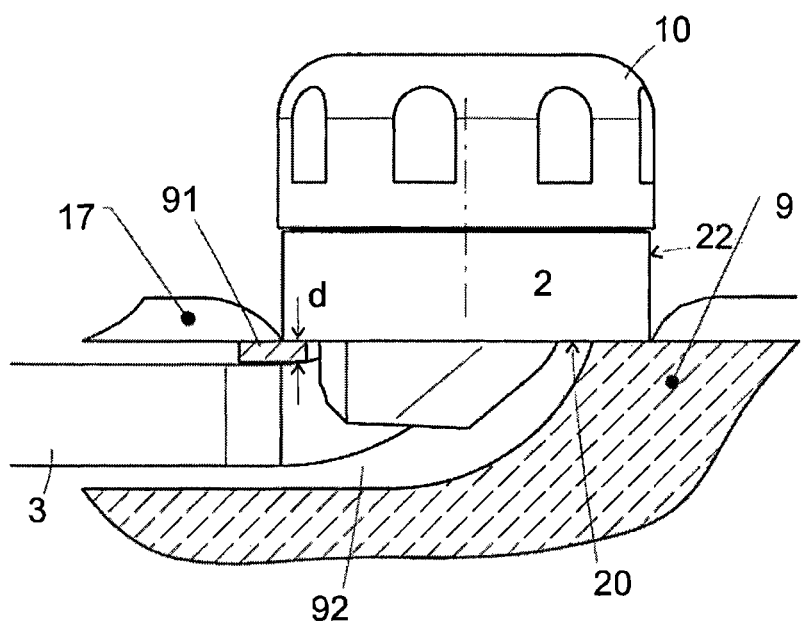
FIG. 7 shows the access port including a protective cap and being implanted in bone, according to an embodiment.

In FIG. 7, the coupling member 2 is represented implanted in the bone 9 with the outlet nozzle 24 being fully buried in the bone 9. An internal conduit 3 extends through the outlet nozzle 24 and in a trench 92 provided in the bone 9. The internal conduit 3 extends from the outlet nozzle 24 at a distance d underneath the base plate 20 such as to leave a bone portion 91 between the base plate 20 and the internal conduit 3. In this configuration, bone 9 can contact the coupling member 2 along its whole periphery. The skin 17 can then be in contact only with the bone 9 and possible passages or grooves between the skin 17 and the first coupling member 2 are avoided, thus decreasing the risk of infection. The spacing d can be typically greater than 1 mm to allow for the bone portion 91 between the base plate 20 and the internal conduit 3 to have a thickness such as to be structurally solid enough.

The coupling member 2 comprises a first valve system as represented by numeral 7 in FIG. 1. In this example, the first valve system 7 comprises a cylindrical inner core 73 rotatably mounted within the coupling member 2. The inner core 73 comprises a valve conduit, here two passageways 70, 71, extending through it. When the first valve system 7 is in an open configuration, the inner core 73 is rotated in a position where the two passageways 70, 71 are aligned with the outlet nozzle 24, allowing fluid communication to and from the internal conduit 3. When the first valve system 7 is in a closed configuration, the inner core 73 is rotated in another position where the fluidic communication between the two passageways 70, 71 and the internal conduit 3 is blocked.

The access port 1 can be connected to the proximal end of the internal conduit 3, for example via the outlet nozzle 24. The distal end of the internal conduit 3 is destined to be connected to a vascular structure of the patient, directly or via a lumen. In the embodiment of FIG. 1, the internal conduit 3 comprises two internal access lines 30, 31. For example, the internal conduit 3 can be a catheter for removal and/or return of fluids such as blood in a hemodialysis application. In the open configuration of the first valve system 7, the two passageways 70, 71 are respectively aligned with the two internal access lines 30, 31 of the internal conduit 3. In the closed configuration, the inner core 73 is rotated in a position where none of the two passageways 70, 71 are in fluidic communication with the internal access lines 30, 31.

More particularly in the embodiment of FIG. 1, the first valve system 7 further comprises a valve housing 75 in which the second cylindrical inner core 73 is rotatably mounted and destined to be removably fixed to the coupling member 2. Here, the inner core 73 is mounted into the valve housing 75 with two opposed locking lugs 819 engaging with a guiding flange 819'. The inner core 73 can be placed within (or removed from) the valve housing 75 by aligning the two locking lugs 819 with two corresponding recesses 705 provided at the first valve housing periphery.

Fixation of the valve housing 75 fixed to the coupling member 2 can be provided by screwing an upper thread 78 provided at the outer periphery of the valve housing 75, into a corresponding inner thread 25 provided in the inner side of the wall portion 22. The valve housing 75 can also comprise a lower flange 77 abutting against the base plate 20 when the valve housing 75 is being fixed to the coupling member 2. Here, a connection member 23 extending distally from the valve housing 75 is used for connecting the internal conduit 3 such that, when the valve housing 75 is fixed to the coupling member 2, the connection member 23 and the internal conduit 3 extend within the outlet nozzle 24.

In the embodiment of FIG. 1, the coupling member 2 further comprises a second valve system 8. Here, the second valve system 8 is a membrane valve comprising a first and a second sealing membrane 80, 81. The second valve system 8 can be removably connected to the first valve system 7. In the example of FIG. 1, the two sealing membranes 80, 81 are disposed in a second valve housing 85 having an outer shape adapted to fit tight within at least a portion of the first and second passageways 70, 71 of the inner core 73. Alternatively, the two sealing membranes 80, 81 and the second valve housing 85 can be made in a single piece. The sealing membranes 80, 81 can also be inserted directly within at least a portion of the passageways 70, 71. The second valve system 8 can be lockingly connected to the first valve system 7 using the clipping member 814. For example, the first and second sealing membranes 80, 81 can be press-fit into the passageways 70, 71. Here, the clipping member 814 can comprise locking members 815 destined to cooperate with a groove 824 such as to achieve a releasably-clipped engagement with the first valve housing 75. The clipping member 814 is provided with openings 818 allowing accessing the two sealing membranes 80, 81. The interface between the connected first and second valve systems 7, 8 can be made fluidly and air tight.

Figure 4:
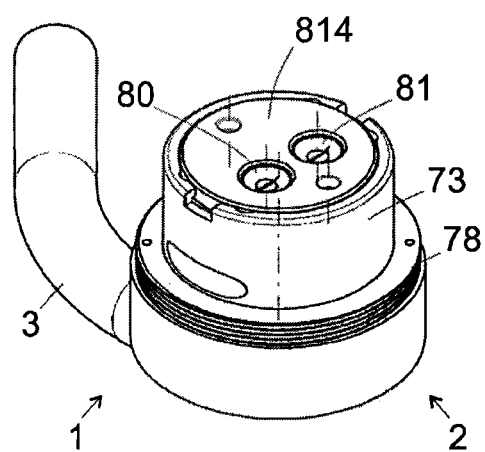
FIGS. 4 and 5 illustrate the assembled access port with the first valve system being in an open and closed configuration, respectively.
Figure 5:
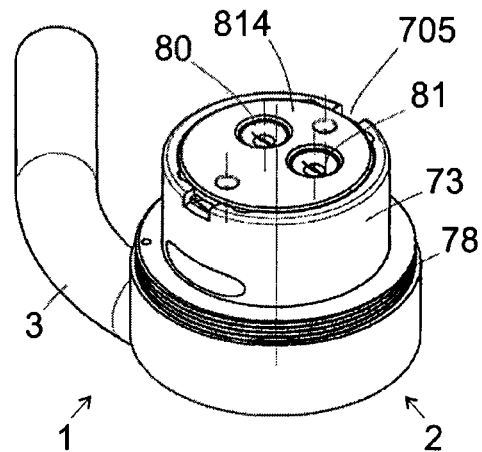

The assembled access port 1 with the coupling member 2 connected to the first and second valve systems 7, 8 is represented in FIGS. 4 and 5. More particularly, in FIG. 4 the access port 1 is shown with the first valve system 7 in the open configuration, the inner core 73 being rotated in a position where the two passageways 70, 71 are aligned with the two internal access lines 30, 31. In FIG. 5, the access port 1 is shown with the first valve system 7 in the closed configuration, the inner core 73 being rotated in a position where the two passageways 70, 71 are not fluidly in communication with the internal access lines 30, 31.

Figure 6:
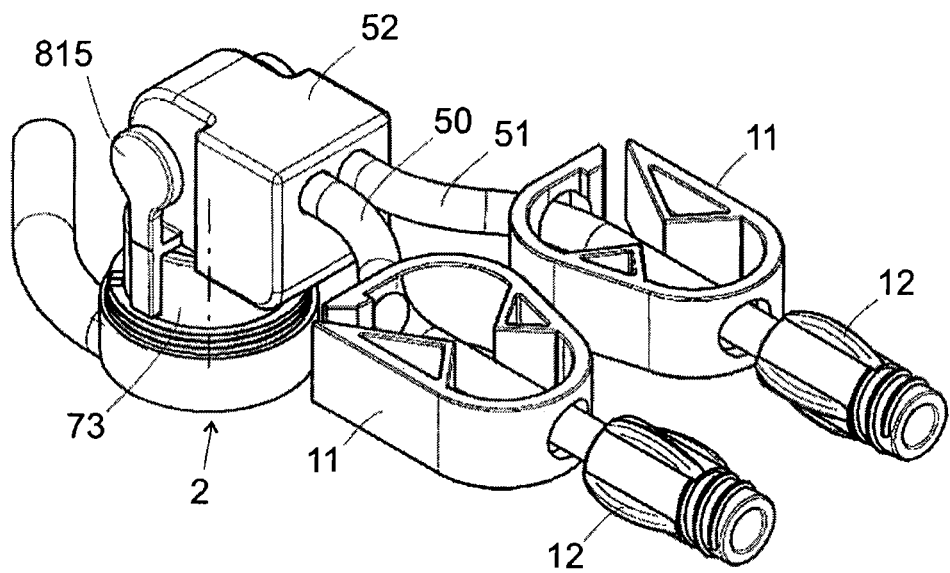
FIG. 6 represents the access port connected to an external conduit according to an embodiment.

As illustrated in FIG. 6, the access port 1 can be connected the distal end of an external conduit 5. The second valve system 8 is being operated in the open configuration when the external conduit 5 is inserted through the sealing membranes 80, 81, and in the closed configuration when the external conduit 5 is removed from the sealing membrane 80. In the open configuration, fluidic communication is established to and from the external conduit 5 and being blocked in the closed configuration.

In the example of FIG. 6, the external conduit 5 comprises two external access lines 50, 51, the external conduit 5 being connected to the access port 1 by inserting the proximal end of the external access lines 50, 51 (not visible in FIG. 6) in the respective sealing membranes 80, 81. As shown in FIG. 6, the external conduit can be fixed to the access port 1 via an external connecting member 52. Here, the external connecting member 52 comprises locking members 815 adapted to engage with an upper guiding flange 815' of the valve housing 75, achieving a releasably-clipped connection of the external connecting member 52 with the port 1. The external access lines 50, 51 are also shown with conventional clamps 11 used for opening and closing the respective lines 50, 51. The distal end of the external access lines 50, 51 can be provided with luer connectors 12 for coupling with the extracorporeal device such as hemodialysis equipment (not shown).

The sealing membranes 80, 81 can be made with a thickness and from a suitable material such as to provide sufficient flexibility to allow the sealing membranes 80, 81 to open when the external conduit 5 is inserted into them and close sealingly for air and fluids when the external conduit 5 is removed from the sealing membranes 80, 81. Suitable materials include biocompatible elastomers such as silicone rubber, polymers, or self-repairing polymers. Each sealing membrane 80, 81 can be provided with a preformed passage 802 (see FIG. 1) extending through it and in which the proximal end of the external access lines 50, 51 can be inserted.

The fluid communication is established between the internal conduit 3 and the external conduit 5 being connected to the access port 1, when the first and second valve systems 7, 8 are connected and in the open configuration.

When the access port 1 is not in use and the external connection 5 is not connected to it, a protective cap 10 can be fixed on the access port 1, as shown in FIG. 7. The cap 10 can be fixed by screwing it on the upper thread 78 extending above the wall portion 22 of the coupling member 2 or by any other means including by clipping. When screwed, the cap 10 closes sealingly the first and second valve systems 7, 8. The cap 10 can further include a sealing pad on its inner surface (not shown), possibly containing a disinfecting substance. Alternatively, or in addition to the sealing pad, a protecting foil (also not shown) can be placed on top of port 1, sealingly covering the second valve system 8, protecting it when the protective cap 10 is removed.

In an embodiment, the access port 1 can be assembled by passing the internal conduit 3 through the outlet nozzle 24 of the coupling member 2, connecting the internal conduit 3 to the connection member 23 of the first valve system 7, fitting the sealing membranes 80, 81 to first valve system 7, for example within the passageways 70, 71, and fixing the first valve system 7, connected to the second valve system 8, to the coupling member 2. Assembling the access port 1 can further comprise the step of mounting the inner core 73 in the valve housing 75.

Figure 8:
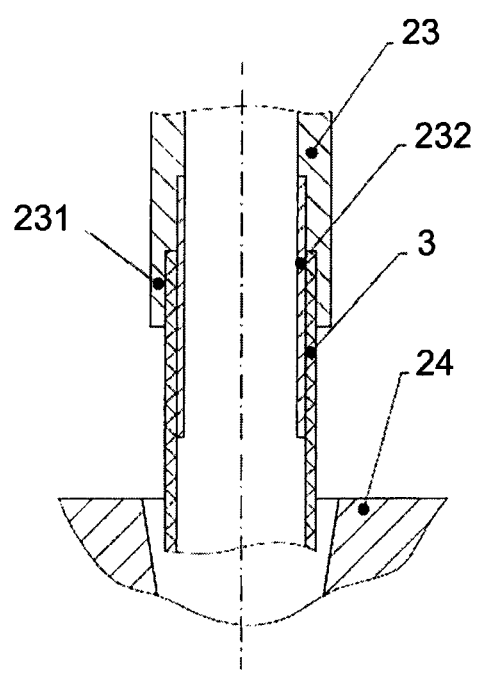
FIGS. 8 and 9 illustrate an arrangement of the connection member of the second coupling member according to an embodiment.
Figure 9:
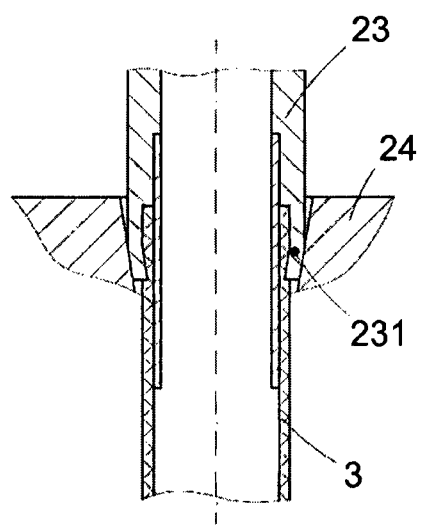
Figure 10:
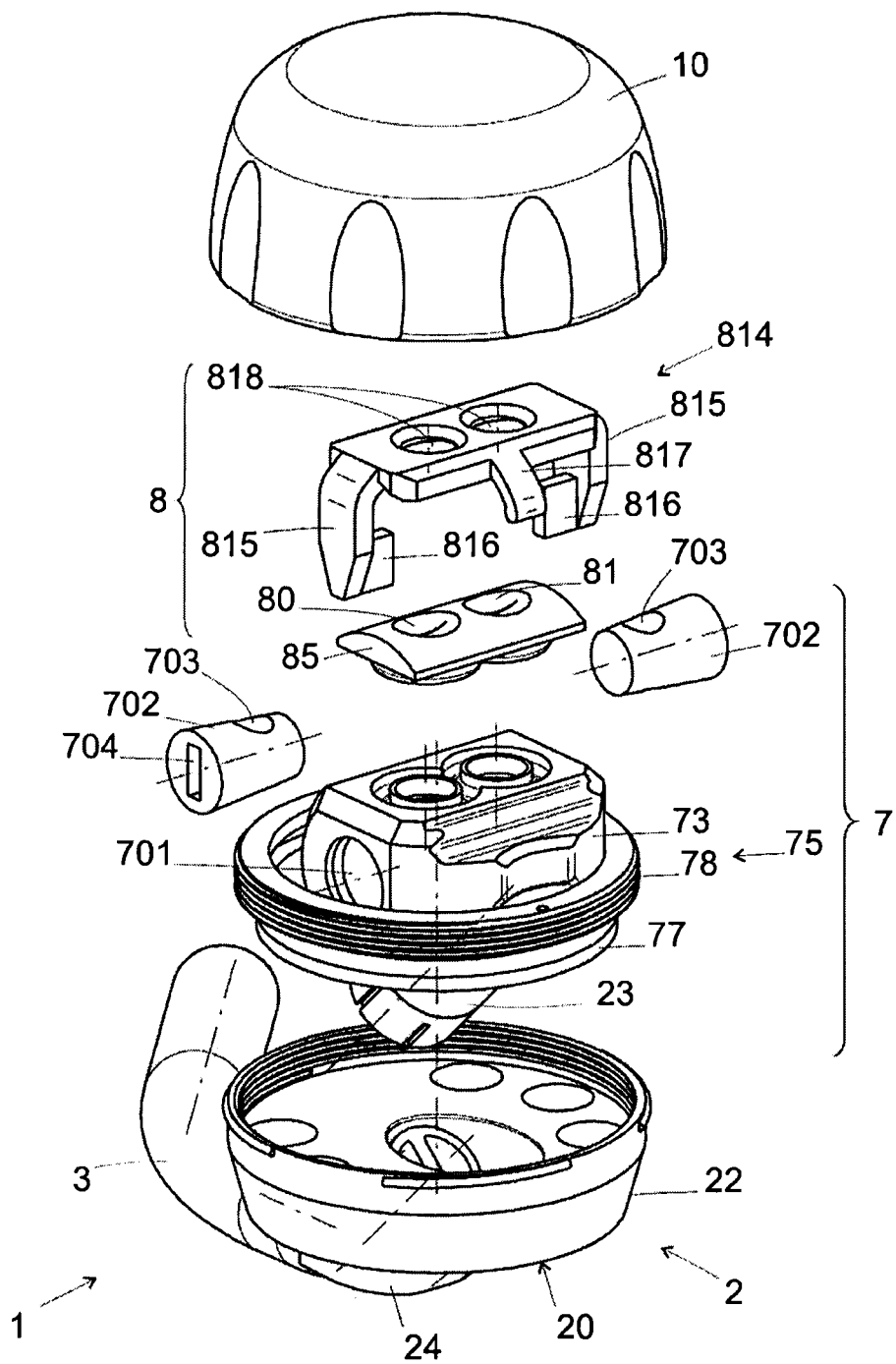
FIG. 10 represents an exploded view of the access port according to another embodiment.

FIGS. 8 and 9 illustrate a possible arrangement of the connection member 23 and the outlet nozzle 24. Here, the distal end of the connection member 23 comprises an inner sleeve portion 232 and flexible blades 231 arranged such that the internal conduit 3 can be slipped on the distal end of the connection member 23, between the inner sleeve portion 232 and the flexible blades 231. When the valve housing 75 is mounted in the coupling member 2, the connection member 23 engages within the outlet nozzle 24 and the tapered inner wall of the outlet nozzle 24 compresses the internal conduit 3 against the connection member 23, between the flexible blades 231 and the sleeve portion 232, locking the internal conduit 3 to the connection member 23. In a variant of the embodiment, the connection member 23 does not comprise the flexible blades 231. Here, the internal conduit 3, slipped on the distal end of the connection member 23, is compressed against the connection member 23, between the inner wall of the outlet nozzle 24 and the connection member 23.

Other connection arrangements of the connection member 23 are also possible. For example, the connection member 23 can have a tapered outer distal portion (not shown). The internal conduit 3 can be locked in its connected position by using clamping structures (not represented) or by gluing, or the like. Barbs (also not shown) can be provided on the outer surface of the connection member 23. Alternatively, the connection member 23 can comprise a pipe coupling connector, such as a threaded coupling, basquill lock and the like.

Figure 11:
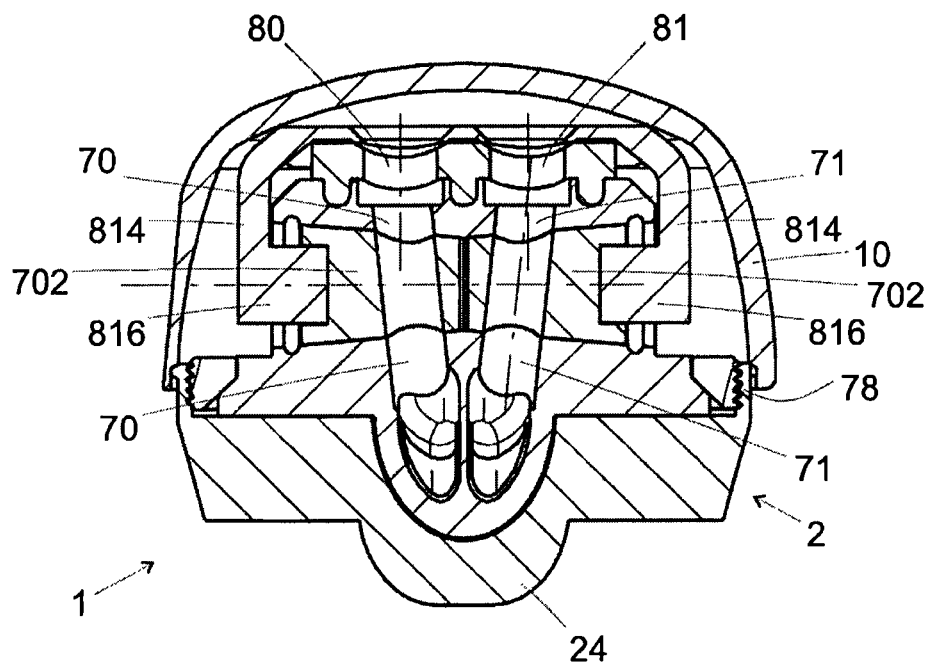
FIG. 11 is a cross-section view of the access port according to the embodiment of FIG. 10.

FIGS. 10 to 13 represent the access port 1 according to another embodiment. Here, the inner core 73 of the first valve system 7 can be mounted non-rotatably in the valve housing 75. Here, the inner core 73 comprises a first and second passageway 70, 71 aligned and in fluidic communication with the internal aperture, or connection member 23, thus with the internal access lines 30, 31 when the internal conduit 3 is connected to the access port 1. The inner core 73 is further provided with two lateral bores 701, each lateral bore 701 extending perpendicular to the passageways 70, 71. A plug 702 comprising a traversing channel 703 is rotatably mounted in each lateral bore 701. In the open configuration, the plugs 702 are rotated in a position where the channel 703 is aligned with the corresponding passageway 70, 71, establishing fluidic communication to and from the internal conduit 3. In the closed configuration, the plugs 702 are rotated in a position where fluidic communication to and from the internal conduit 3 is blocked. The cross-section view of FIG. 11 shows the two channels 703 extending through each of the plugs 702 in the open configuration. The inner core 73 can further comprise a shunting passageway (not shown) fluidly shunting the passageways 70, 71 when the inner core 73 is in the closed position. Such shunting passageway can be useful for passing a cleaning fluid within the passageways 70, 71 when the first valve system 7 is in the closed configuration.

Figures 12, 13:
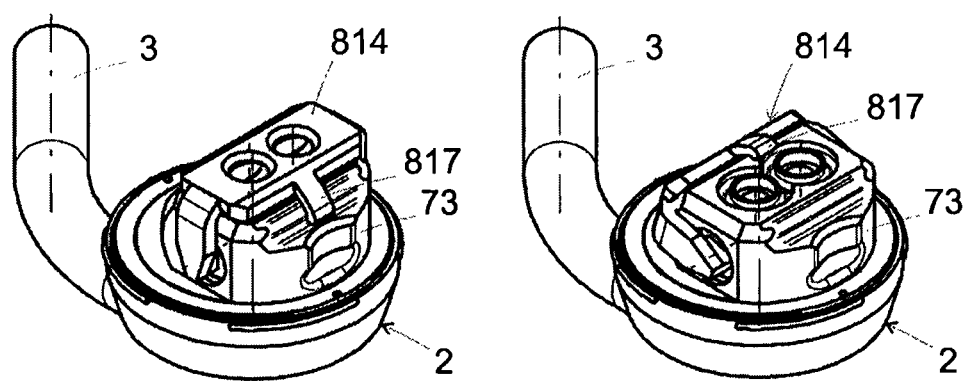
FIGS. 12 and 13 show the access port according to the embodiment of FIG. 10 comprising a clipping member shown in a clipped and unclipped configuration, respectively.

In the example of FIGS. 10 to 13, the second valve system 8 is formed from a low profile second valve housing 85 comprising the two sealing membranes 80, 81, and is fitted on the top side of the inner core 73. The second valve system 8 can be lockingly connected to the first valve system 7 using the clipping member 814. More particularly, the sealing membranes 80, 81 can be lockingly press-fitted within at least a portion of the passageways 70, 71 of the inner core 73 with the clipping member 814. Here, the clipping member 814 comprises two locking member 815 provided with a protruding part 816, adapted to fit into a tool slot 704 provided on the outer end of each plug 702. The protruding parts 816 exert a lateral force on each plug 702 ensuring a good sealing between the plug 702 and the lateral bore 701. The clipping member 814 can further comprise a lock finger 817 adapted to locks the clipping member 814 to the inner core 73 in its press-fitting position as shown in FIG. 12 and keeping the plugs 702 in the open configuration. By unclipping the lock finger 817, the clipping member 814 can be rotated about the rotation axis of the plugs 702. The rotational movement of the clipping member 814 causing the plugs 702 to be rotated with it. FIG. 13 shows the clipping member 814 is a position where the plugs 702 are in the closed configuration. In this configuration, the second valve housing 85 with the two sealing membranes 80, 81 can be removed from the inner core 73, for example, for cleaning or replacing the sealing membranes 80, 81. Directional indicators (not shown) for indicating the closed and open positions of the valve 7 can be comprised on the external surface of the plug 702 or of the valve housing 75.

Other conformations of the clipping member 814 are also possible provided the clipping member 814 can operate the first valve system 7 in the open or closed configurations when the clipping member 814 lockingly connects the second valve system 8 to the first valve system 7, and operate the first valve system 7 in the closed configuration when the clipping member 814 is unclipped, allowing for disconnecting the second valve system 8 from the first valve system 7.

Figure 14:
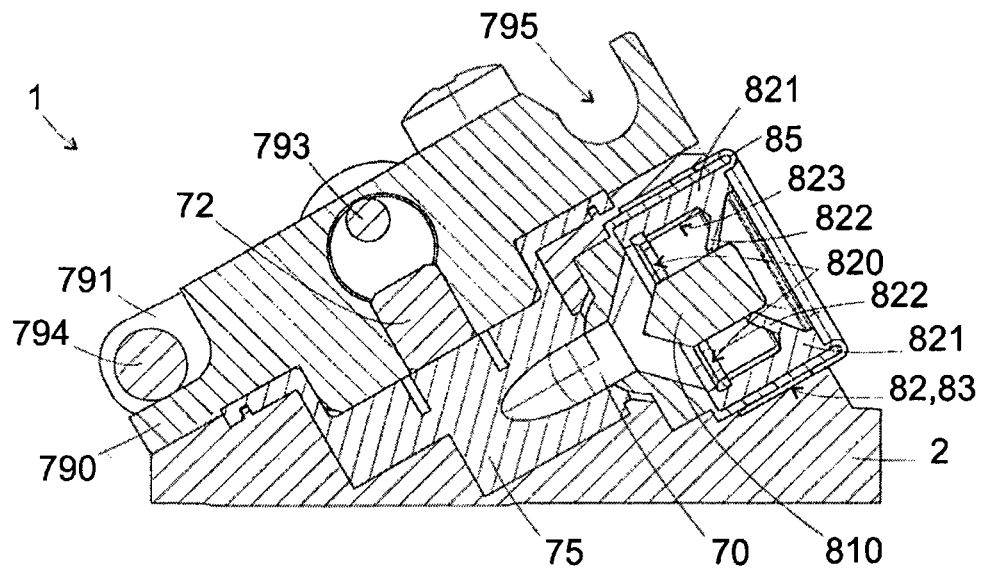
FIG. 14 shows a cross-section view of the access port according to yet another embodiment.
Figure 15:
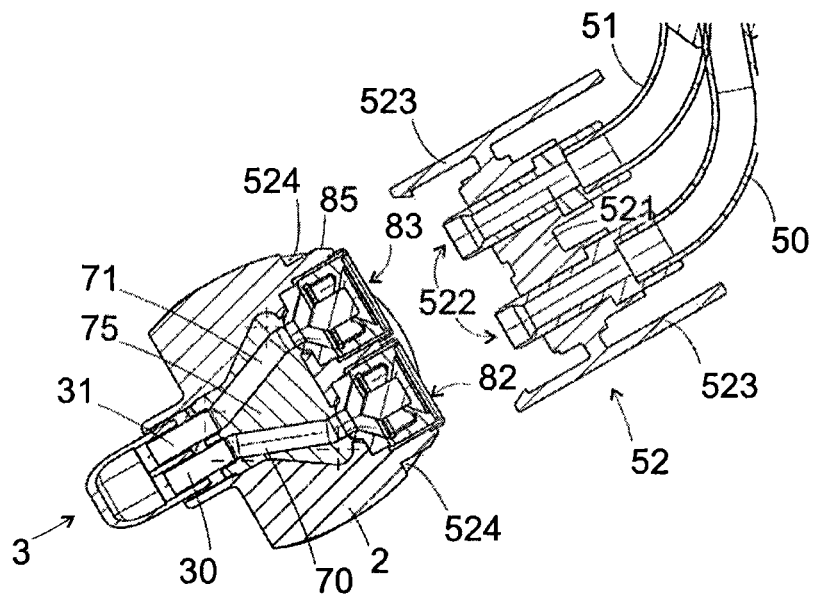
FIG. 15 shows a top view of the access port according to the embodiment of FIG. 14 and an external connecting member according to an embodiment.
Figure 16:
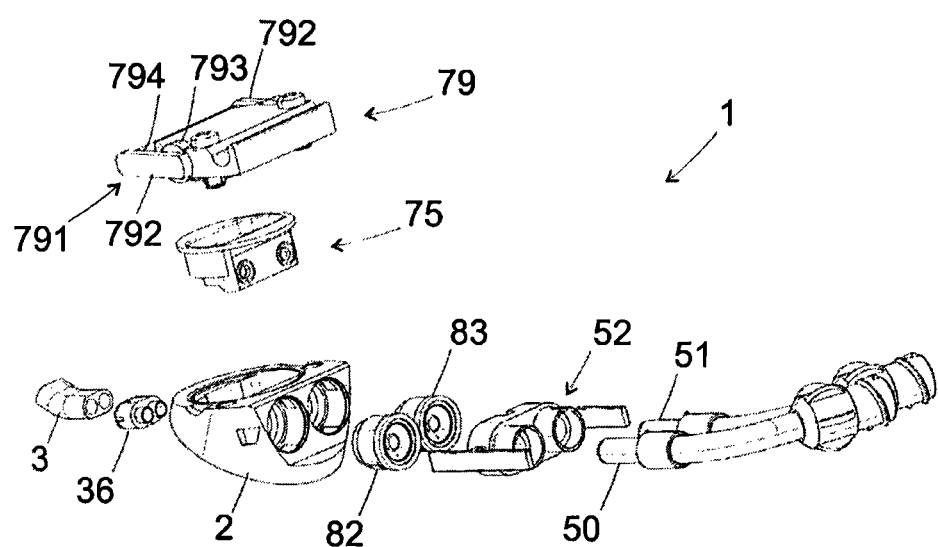
FIG. 16 shows an exploded view of the access port according to the embodiment of FIG. 14.

FIGS. 14 to 16 illustrate the access port 1 according to yet another embodiment. More particularly, FIG. 14 represents a cross-section, FIG. 15 a top view and FIG. 16 an exploded view of the access port 1. In this embodiment, the first valve system 7 comprises a resilient valve conduit, here two resilient passageways 70, 71, and a clamping device, here a plunger 72, arranged in the first coupling member 2 (only one passageway and one plunger are visible in FIG. 14). When the first valve system 7 is in the closed configuration, the plunger 72 is arranged such as to compresses the passageways 770, 71 collapsing it closed. In the open configuration, the plunger 72 is arranged such as to release the pressure and allow the passageways 70, 71 to regain their open configuration. Here, the plunger 72 is movable substantially perpendicularly with the passageways 70, 71, downwardly in the closed configuration and upwardly in the open configuration. In the example of FIGS. 14 to 16, the resilient passageways 70, 71 are fitted in the valve housing 75 and are fluidly connected to the two internal access lines 30, 31, respectively. Alternatively, the clamping device can comprise two plungers 72, each plunger being adapted to apply a pressure on one of the two passageways 70, 71 in the closed configuration. In the examples of FIGS. 14 to 16, the two passageways 70, 71 extend in the access port 1 making a small angle with the base plate 20 such as to minimize the height of the port 1. As shown in FIG. 16, the internal conduit 3 can be connected to the first valve system 7 via a connecting part 36.

In the example of FIGS. 14 to 16, the plunger 72 is moved via a lever mechanism 79 placed on top of the valve housing 75. More particularly, the lever mechanism 79 comprises a lever plate 790 on which a lever 791 is pivotally mounted about a hinge 793. The lever 791 is formed from two lever arms 792 and a bar 794 extending between the two lever arms 792, perpendicular to the lever arms 792. The lever 791 is mounted eccentrically in the hinge 793 such that in the open position, shown in the FIG. 14, the hinge 793 is positioned away from the plunger 72, keeping it in its upper position such that the passageways 70, 71 are in their fluidly open configuration. When the lever 791 is pivoted in the closed position, in which the bar 794 is positioned into a groove 795 provided in the lever plate 790, the hinge 793 is displaced downwardly depressing the plungers 72 such as to fluidly close the passageways 70, 71.

Referring to FIGS. 14 and 15, the second valve system 8 is formed from a first and second pivot valve 82, 83, each pivot valve 82, 83 being fitted in the second valve housing 85 that can be removably fixed into the valve housing 75. More particularly, each pivot valve 82, 83 comprises a pivot 810 concentrically held in a pivot sleeve 823 containing a pivot base 820 provided with openings 818 for the passage of fluids at its proximal end. The pivot valve 81 further comprises a sealing sleeve 821 having sealing lip 822 placed concentric with the pivot 810 such that the sealing lip 822 can sealingly engage around the pivot 810.

The external connecting member 52 destined to be connected to the access port 1 is shown in FIG. 15 according to another embodiment. Here, the external connecting member 52 comprises a connecting housing 521 and two connecting elements 522 from which the two external access lines 50, 51 extend distally, and destined to be connected to the respective pivot valves 81 of the second valve system 8. The external connecting member 52 further comprises clipping arms 523, two in the example of FIG. 15, adapted to be releasably clipped with the access port 1, for example with clipping grooves 524 provided in the first coupling member 2. Prior to connecting the external connecting member 52 to the access port 1, as shown in FIG. 15, the sealing lip 822 of each pivot valve 82, 83 engage sealingly around the pivot 810 and the second valve system 8 is in the closed position. After connecting the external connecting member 52 to the access port 1, the proximal end of each connecting element 522 press on the respective sealing lip 822 such as to disengage it from the pivot 810, opening fluidly the pivot valve 82, 83. In this open position, the fluid can flow between the external access lines 50, 51 and the first and second passageways 70, 71.

In another embodiment not represented, each pivot valve 82, 83 comprises a movable pivot and an annular seal cooperating with the pivot. In the closed position of the valve 8, the movable pivot is biased towards the annular seal resulting in fluid-tight connection between the pivot and the annular seal. Upon connecting the two external access lines 50, 51 to the second valve system, the proximal end of the external access lines 50, 51 axially displaces the corresponding movable pivot, away from its corresponding annular seal, setting the movable pivot in the open position. The movable pivots can be biased on the annular seal by a pressure spring, for example by a spiral pressure spring, or any other biasing means. The two annular seals can be made of suitable elastomeric material or any other resilient material and held in an annular recess in the first valve housing 85. The retaining of the annular seals in the recess can be performed by adhering, force fit, a spring ring or the like.

Figure 17:
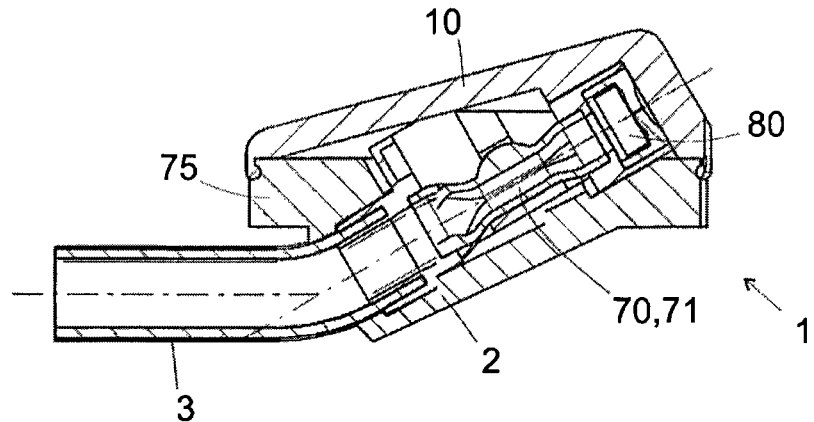
FIG. 17 shows a cross-section view of the access port according to yet another embodiment.
Figure 18:
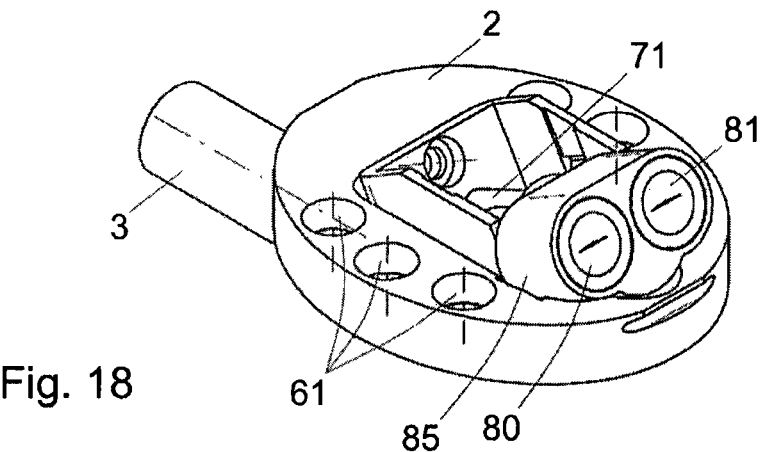
FIGS. 18 and 19 represent a perspective view of the access port according to the embodiment of FIG. 17.
Figure 19:
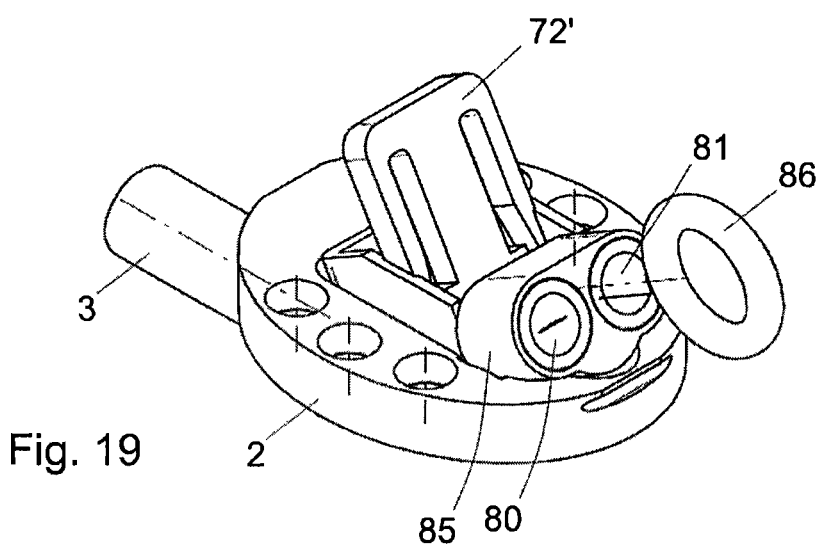

FIGS. 17 to 19 show a cross-section view of the access port 1 according to yet another embodiment. In this configuration, the resilient passageways 70, 71 are directly fitted within the first coupling member 2 and connected to the proximal end of the internal conduit 3 and the second valve system 8. The clamping device is a loose plunger 72'. As shown in FIG. 19, the sealing membranes 80, 81 can be removed from the second valve housing 85 by using a tool 86, adapted to be inserted through the preformed passage 802 of the membrane valve 80. In a variant, the loose plunger 72' can be clipped to the coupling member 2 such as to remained fixed the closed configuration where it apples a pressure on the passageways 70, 71 for closing them.

Figure 20:
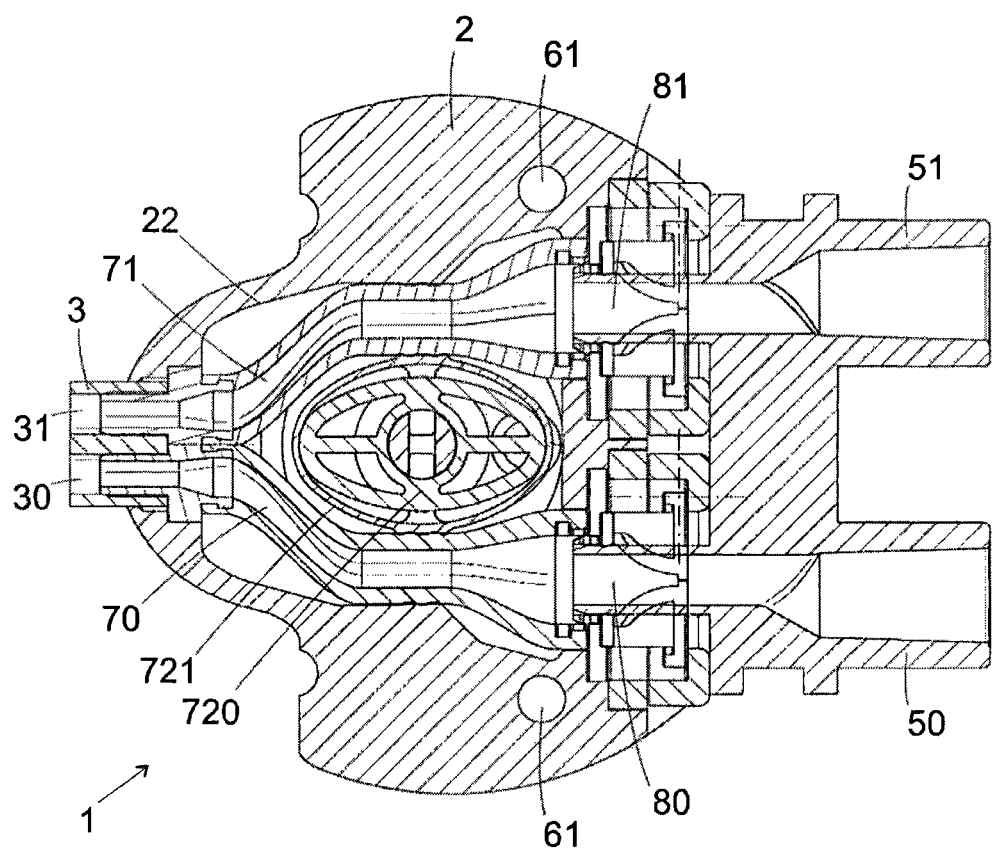
FIG. 20 illustrates a cross-section view of the access port according to yet another embodiment.

In yet another embodiment represented in FIG. 20, the clamping device comprises a rotatable cam 720 arranged in the first coupling member 2 such that the cam 720 can rotate in a position where it collapse the passageways 70, 71, setting the first valve system 7 in the close configuration, and in another position where the passageways 70, 71 can open, setting the first valve system 7 in the open configuration. In the example of FIG. 20, the cam 720 has an elliptical shape such that, when the first valve system 7 is in the closed configuration, the long axis of the cam 720 is rotated substantially perpendicular to the passageways 70, 71 and the cam 720 collapse the passageways 70, 71 fluidly closed against the wall portion 22. In the open configuration, the long axis of the cam 720 is substantially parallel to the longitudinal direction of the passageways 70, 71, such that they remain fluidly open. The clamping device can further comprise a resilient ring 721 concentric with the cam 720. In the closed configuration, the long axis of the cam 720 presses against the resilient ring 721 extending it against the wall portion 22, collapsing the passageways 70, 71 fluidly closed.

Figure 21:
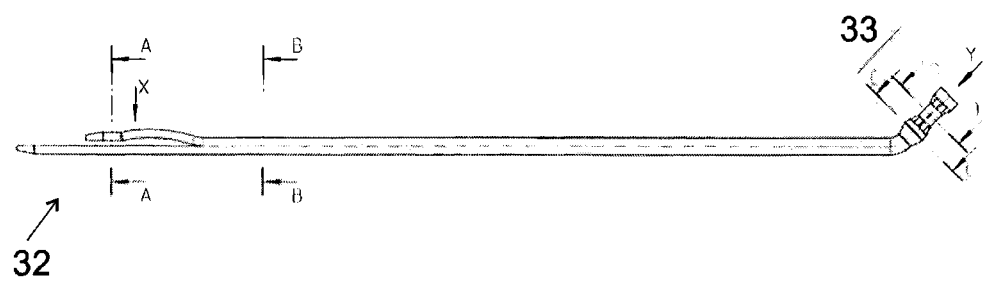
FIG. 21 illustrates an internal conduit according to an embodiment.
Figure 22:
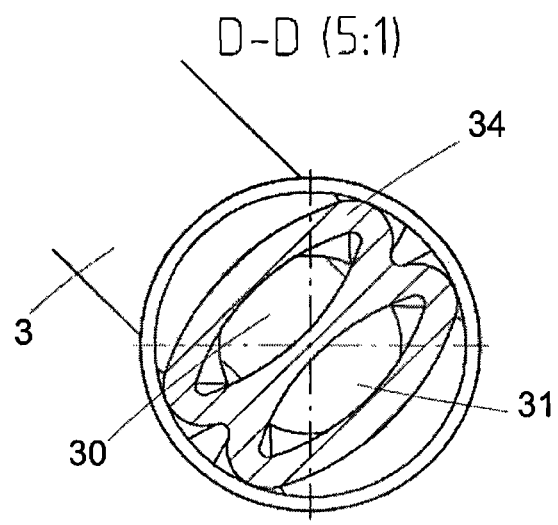
FIG. 22 shows a cross section of the internal conduit 3 according to the embodiment of FIG. 21.

In yet another embodiment, the internal conduit 3 is connected to the second valve system 8 and the resilient valve conduit comprises a proximal portion 33 of internal conduit 3 (see FIG. 21). In the closed configuration of the first valve system 7, the clamping device 72, 72', 720 collapses fluidly closed the proximal portion 33. In this configuration, the access port 1 comprises only one connection interface, where the internal conduit 3 connects the second valve system 8, thus minimizing possible contamination of the access port 1. FIG. 21 illustrates the internal conduit 3 containing the two internal access lines 30, 31, according to an embodiment. The distal end 32 of the internal conduit 3 is destined to be connected to the heart of the patient and its other end (proximal end) to the access port 1. The stiffness of conventional internal conduits, or catheters, is typically high such as to avoid the internal conduit to self-collapse in use. Fluidly closing such conventional internal conduits with the clamping device 72, 72', 720 can thus be difficult and unreliable. Here, the proximal portion 33 is made more resilient than the remaining of the internal conduit 3 in order to collapse the proximal portion 33 more easily and in a more reliable fashion. FIG. 22 shows a cross section of the internal conduit 3 along the sections D-D and of FIG. 21, across the proximal portion 33. As seen in FIG. 22, the wall 34 of internal access lines 30, 31 has an oval shape with its long axis being oriented substantially perpendicular to the direction in which the internal conduit 3 is compressed by the clamping device 72, 72', 720. Moreover, the thickness of the wall 34 can be made thinner along the proximal portion 33 than along the rest of the internal conduit 3. A higher resilience of portion 33 can then be achieved compared with the resilience of the rest of the internal conduit 3. Additionally or alternatively, the proximal portion 33 can be made of a material having a higher resilience than the rest of the internal conduit 3.

Figure 23:
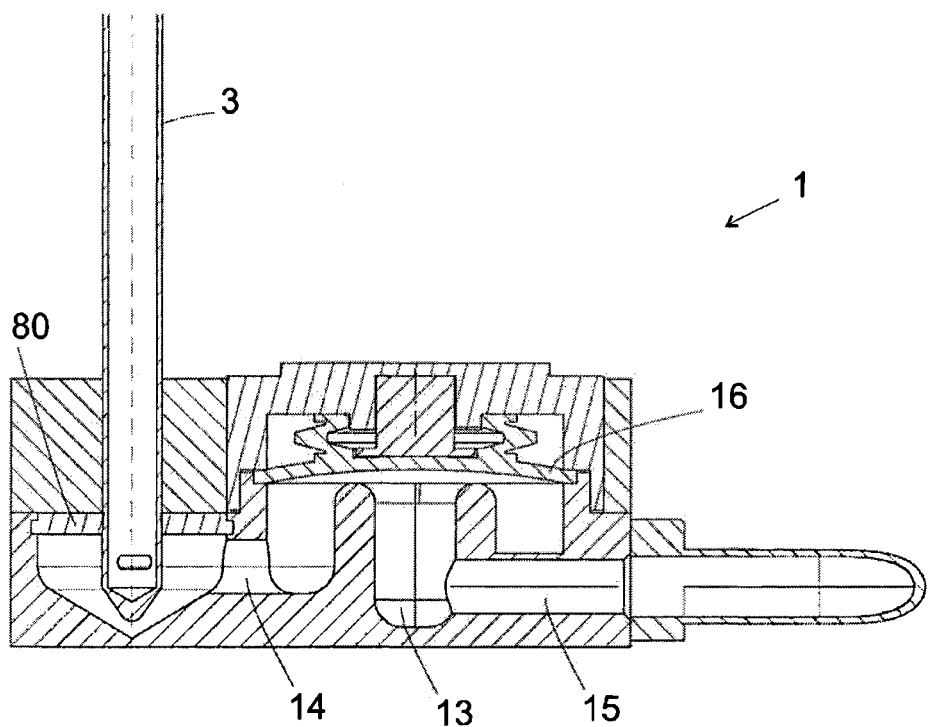
FIG. 23 represents the access port according to yet another embodiment.

FIG. 23 illustrates the access port 1 according to yet another embodiment. Here, the first valve system 7 comprises a diaphragm valve including a pump chamber 13 in communication with an inlet 14 and an outlet 15, and a flexible diaphragm 16. The diaphragm 16 is adapted to move from the open position to the closed position, where the open position permits the fluid to flow through the inlet 14, the pump chamber 13 and outlet 15, and, in the closed position to block the fluid flow. FIG. 23 also shows the membrane valve 80 connected to the external conduit 5.

Figure 24:
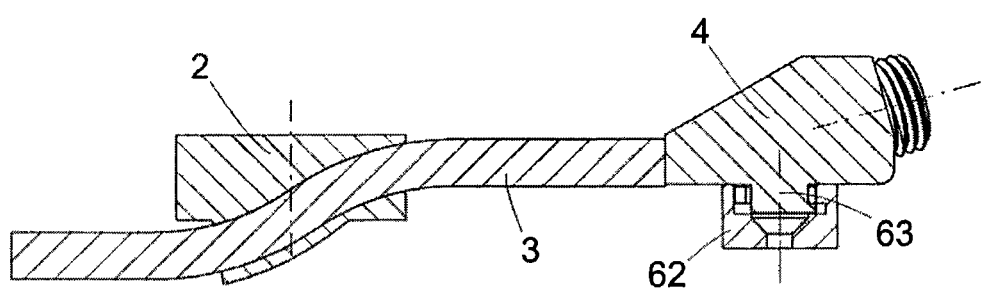
FIG. 24 shows the access port comprising a second fixation unit, according to yet another embodiment.

In an embodiment illustrated in FIG. 24, the coupling member 2 further comprises an auxiliary coupling member 4 destined to be anchored in a tissue of the patient remotely form the coupling member 2 and comprising the second valve system 8. In the example of FIG. 24, the anchoring of the auxiliary coupling member 4 is performed via an auxiliary fixation unit 62. The auxiliary fixation unit 62 comprises an attachment device 63, for example a snap button, allowing for detachably fix the auxiliary coupling member 4 to the auxiliary fixation unit 62. In the configuration of FIG. 24, the internal conduit 3 extends through the first and second coupling members 2, 4 and is connected to the second valve system 8.

The disclosure is susceptible to various modifications and alternative forms, and specific examples thereof have been shown by way of example in the drawings and are herein described in detail. It should be understood, however, that the disclosure is not to be limited to the particular forms or methods disclosed, but to the contrary, the disclosure is to cover all modifications, equivalents, and alternatives.

For example, the access port 1 disclosed herein can be used with the internal conduit 3 and the external conduit 5 containing only one or more than two internal and external access lines 30, 31, 50, 51, respectively. For example, an application requiring only one internal access line and one external access line may be used for urinary catheterism where fluid is removed only. Here, the first valve system 7 can comprises respectively one passageway or more than two passageways 70, 71, in accordance with the number of internal and/or external access lines 30, 31, 50, 51. Similarly, the second valve system 8 can comprise one membrane valve 80 or more than two membrane valves 80, 81, in accordance with the number of internal and/or external access lines 30, 31, 50, 51, to provide one passageway and membrane valve 80 per internal and/or external access line 30, 31, 50, 51.

Obviously, the access port 1 can alternatively be connected to more than one external conduit 5 and more than one internal conduit 3, each comprising one or more separate internal or external access lines, respectively. Moreover, the second valve system 8 can be formed by any other type of valve than the membrane valves 80, 81, 82, 83, provided the second valve system 8 can be operated in the open and close configuration when the external conduit 5 is respectively connected to and disconnected from the valve 8. A manually operated valve used as the second valve system 8 is however also possible.

Figure 25:
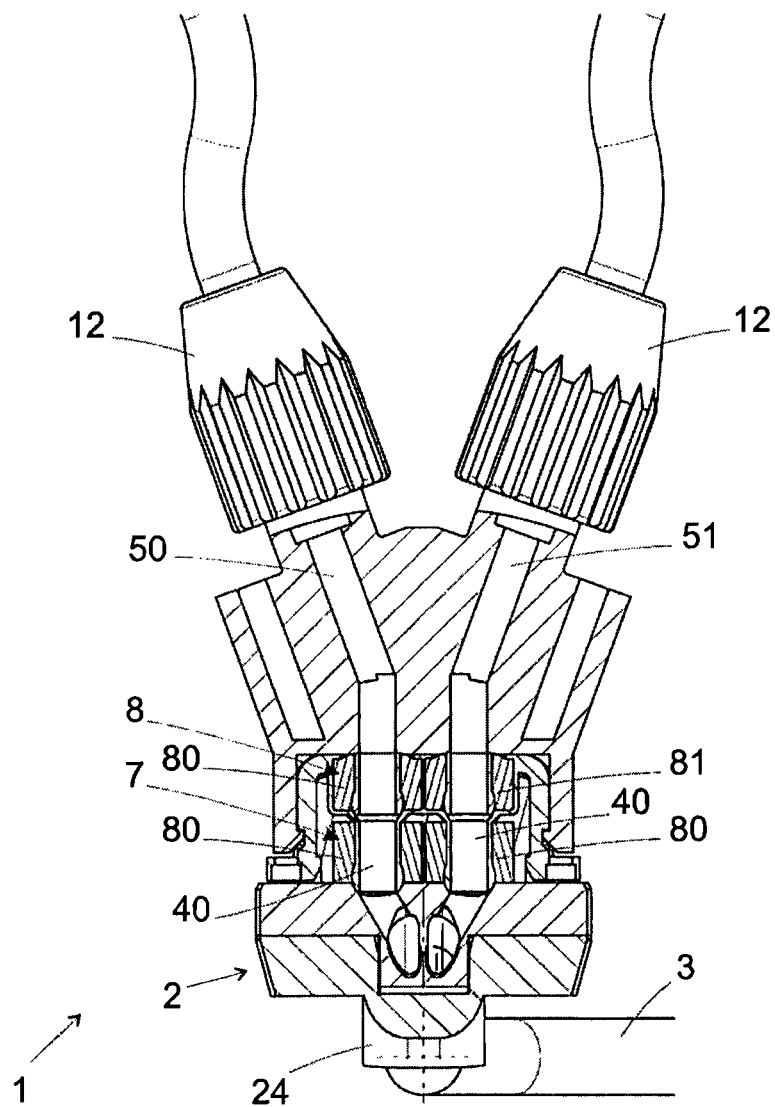
FIG. 25 represents the access port according to yet another embodiment.

FIG. 25 represents the access port 1 according to yet another embodiment. Here both the first and the second valve systems 7, 8 are formed from two sealing membranes 80, 81. In the configuration of FIG. 25, the second valve system 8 is arranged to be connectively assembled with the first valve system 7. More particularly, the second valve system 8 comprises sleeves 40 extending proximally and concentric with the sealing membranes 80, 81 of the second valve system 8, and adapted to be inserted within the sealing membranes 80, 81 of the first valve system 7 when the second valve system 8 is connected to the first valve system 7, opening fluidly the sealing membranes 80, 81 of the first valve system 7. The sealing membranes 80, 81 of the first valve system 7 are sealingly closed when the second valve system 8 is disconnected. As discussed above, the first valve system 7 can be in the open and closed configuration, respectively by connecting and disconnecting the internal conduit 3, and the second valve system 8 can be in the open and closed configuration respectively by connecting and disconnecting the external conduit 5. In the arrangement of FIG. 25, the first valve system 7 in automatically set the open or closed configuration when connecting or removing the second valve system 8 from the access port 1. This is in contrast with the previous embodiments where the first valve system 7 must be set in the closed configuration manually before removing the second valve system 8.

In use, the valve systems 7, 8 of the access port 1 can be operated such that the first valve system 7 is in the closed configuration when the second valve system 8 is disconnected from the first valve system 7. For example, in the embodiments of FIGS. 1, 10, 14, 17, 20, the first valve system 7 have can be operated in the open or closed configuration manually. In the embodiment of FIG. 25, the first valve system 7 is set automatically open when the second valve system 8 is connected to it. In all described configurations, the second valve system 8 is set in the closed configuration when the external conduit 5 is disconnected from the access port 1 and reopened when connected. When the external conduit 5 is connected to the second valve system 8, for example, when the port 1 is use for a dialysis operation, the first valve system 7 is in the open configuration. The first valve system 7 can remains in the open configuration even when the external conduit 5 is disconnected, since the second valve system 8 is then in the closed configuration.

An advantage of the access port 1 is that, the second valve system 8 being repeatedly set in the open and closed configurations as the access port 1 is used, can be easily removed from the port 1 for cleaning and/or replacement purposes, while keeping the access port 1 closed via the first valve system 7. The latter valve 7, being rarely set in the open and closed configurations, will tend to last much longer, retarding the time when the access port 1 needs to be replaced compared with conventional access ports.

| Reference Numbers | |
|---|---|
| 1 | implantable access port |
| 10 | protective cap |
| 11 | clamp |
| 12 | luer connector |
| 13 | pump chamber |
| 14 | inlet |
| 15 | outlet |
| 16 | diaphragm |
| 17 | skin |
| 2 | transcutaneous coupling member |
| 20 | base plate |
| 22 | wall portion |
| 23 | connection member |
| 231 | blade |
| 232 | inner sleeve portion of the connection member |
| 24 | outlet nozzle |
| 25 | inner thread |
| 3 | internal conduit |
| 30, 31 | internal access line |
| 32 | distal end of the internal conduit |
| 33 | proximal portion |
| 36 | connecting part |
| 4 | auxiliary coupling member |
| 40 | sleeves |
| 5 | external conduit |
| 50, 51 | external access line |
| 52 | external connecting member |
| 521 | connecting housing |
| 522 | connecting element |
| 523 | clipping arm |
| 524 | clipping grooves |
| 61 | holes |
| 62 | auxiliary fixation unit |
| 63 | attachment device |
| 64 | arm |
| 700 | valve conduit |
| 70 | first passageway |
| 71 | second passageway |
| 72 | plunger |
| 72' | loose plunger |
| 720 | cam |
| 721 | resilient ring |
| 722 | finger |
| 723 | rigid annulus |
| 724 | tooth portion |
| 73 | inner core |
| 75 | valve housing |
| 77 | lower flange |
| 78 | upper thread |
| 79 | lever mechanism |
| 790 | lever plate |
| 791 | lever |
| 792 | lever arm |
| 793 | hinge |
| 794 | bar |
| 795 | groove |
| 701 | lateral bores |
| 702 | plug |

-continued

| Reference Numbers | |
|---|---|
| 703 | channel |
| 704 | tool slot |
| 705 | recess |
| 8 | second valve system |
| 80 | first sealing membrane |
| 81 | second sealing membrane |
| 802 | preformed passage |
| 810 | pivot |
| 814 | clipping member |
| 815 | locking member |
| 815' | upper guiding flange |
| 816 | protruding part |
| 817 | lock finger |
| 7 | first valve system |
| 818 | openings |
| 819 | locking lug |
| 819' | lower guiding flange |
| 820 | pivot base |
| 821 | sealing sleeve |
| 822 | sealing lip |
| 823 | pivot sleeve |
| 824 | groove |
| 822 | sealing lip |
| 823 | pivot sleeve |
| 824 | groove |
| 82 | first pivot valve |
| 83 | second pivot valve |
| 85 | second valve housing |
| 86 | tool |
| 87 | distal extremity of the sealing membrane |
| 9 | bone |
| 91 | bone portion |
| 92 | trench |
| d | distance |

The invention claimed is:

1. Implantable access port for removal and/or return of fluids to a patient, comprising:
    an internal conduit adapted to be connected at its proximal end to the access port and at its distal end to a vascular structure of the patient;
    an external conduit adapted to be connected at its proximal end to the access port and at its distal end to an extracorporeal device; and
    a transcutaneous coupling member destined to be anchored in a tissue of the patient and comprising a first valve system operable to be in an open or closed configuration to establish or block fluidic communication to and from the internal conduit;
    the coupling member further comprising a second valve system adapted to be removably connected to the first valve system and operable to be in an open or closed configuration to establish or block fluidic communication to and from the external conduit, such as to establish fluid communication between the internal and external conduits when the first and second valve systems are connected and in the open configuration.

2. The access port according to the claim 1, wherein the first valve system comprises a resilient valve conduit and a clamping device, the clamping device being adapted to apply a pressure on the resilient valve conduit to collapse it and set the first valve system in the closed configuration, and release the pressure allowing the resilient valve conduit to open, setting the first valve system in the open configuration.

3. The access port according to claim 2, wherein the valve conduit comprises one or several resilient passageways.

4. The access port according to claim 2, wherein the proximal end of the internal conduit is connected to the second valve system and the resilient valve conduit comprises a proximal portion of the internal conduit.

5. The access port according to claim 4, wherein the proximal portion is more resilient than the rest of the internal conduit.

6. The access port according to claim 2; wherein the clamping device is a plunger arranged such as to be movable substantially perpendicularly to the valve conduit.

7. The access port according to claim 2, wherein the clamping device is a rotatable cam arranged such as to rotate in a position where it can collapse the valve conduit when the first valve system is in the closed configuration, and in another position where the valve conduit can open, when the first valve system is in the open configuration.

8. The access port according to claim 1, wherein the first valve system comprises one or several passageways traversingly arranged in an inner core.

9. The access port according to claim 8, wherein the inner core can be rotated in a position where said one or several passageways are in fluidic communication with the internal conduit, setting the first valve system in the open configuration, and in another position where the fluidic communication between said one or several passageways and the internal conduit is blocked, setting the first valve system in the closed configuration.

10. The access port according to claim 9, wherein the first valve system further comprises a valve housing removably connectible to the coupling member and in which the inner core is rotatably mounted.

11. The access port according to claim 8, wherein the inner core further comprises one or several lateral bores, each of them extending substantially perpendicular to and traversing each of said one or several passageways and comprising a plug provided with a traversing channel and rotatably mounted in the lateral bore, such that, when the first valve system is in the open configuration, the plug is rotated to a position where the channel is aligned with one of the passageways, establishing fluidic communication with the internal conduit, and when the first valve system is in the closed configuration, the plug is rotated to another position where fluidic communication between the channel and the valve conduit is blocked.

12. The access port according to claim 11, wherein the first valve system further comprises a connection member destined to be connected to the internal conduit.

13. The access port according to claim 12, wherein the coupling member further comprises an outlet nozzle with which the connection member engages when the first valve system is connected to the coupling member, such that the internal conduit is compressed against the connection member, locking it to the connection member.

14. The access port according to claim 1, wherein the second valve system comprises a membrane valve that can be operated in the open configuration by inserting the proximal end of the external conduit through the membrane valve, and in the closed configuration by removing the external conduit from the membrane valve.

15. The access port according to claim 14, wherein the membrane valve comprises one or several sealing membranes made of a resilient material.

16. The access port according to claim 15, wherein each of said one or several sealing membranes are provided with a preformed passage.

17. The access port according to claim 14, wherein the membrane valve comprises one or several pivot valves each of said one or several pivot valves being formed from a pivot and a sealing lip such that the sealing lip sealingly disengage from the pivot, opening fluidly the pivot valve when the external conduit is inserted, and engage sealingly around the pivot when the external conduit is removed.

18. The access port according to claim 14, wherein the second valve system further comprises a clipping member adapted to be in a first and second position where the second valve system is respectively lockingly connected and disconnected to the first valve system.

19. The access port according to claim 18, wherein the clipping member is arranged to operates the first valve system such as to set it in the open and closed configuration when the clipping member is in the first and second position, respectively.

20. The access port according to claim 1, wherein the coupling member further comprises a fixation unit for anchoring the coupling member to the tissue of the patient.

21. The access port according to claim 20, wherein the fixation unit comprises traversing holes provided in a base plate of the coupling member.

22. The access port according to claim 20, wherein the fixation unit comprises arms provided with traversing holes and attached to the coupling member.

23. The access port according to claim 1, wherein the coupling member further comprises an auxiliary coupling member destined to be anchored in a tissue of the patient remotely from the coupling member and comprising the second valve system.

24. The access port according to claim 23, wherein the fixation unit comprises an auxiliary fixation unit arranged to detachably anchor the auxiliary coupling member to the tissue.

25. The access port according to claim 1, wherein the tissue is a bone.

26. The access port according to claim 25, wherein the bone is any one of: mastoid, temporal or parietal bone.

* * * * *